United States Patent
Olvera et al.

(10) Patent No.: US 12,017,331 B2
(45) Date of Patent: Jun. 25, 2024

(54) TOOL FOR POWERED SPRAYER

(71) Applicant: TECHTRONIC CORDLESS GP, Anderson, SC (US)

(72) Inventors: Eduardo Olvera, Pendleton, SC (US); Graham M. Schaafsma, Raleigh, NC (US)

(73) Assignee: Techtronic Cordless GP, Anderson, SC (US)

( * ) Notice: Subject to any disclaimer, the term of this patent is extended or adjusted under 35 U.S.C. 154(b) by 0 days.

(21) Appl. No.: 17/552,529

(22) Filed: Dec. 16, 2021

(65) Prior Publication Data

US 2022/0212325 A1 Jul. 7, 2022

Related U.S. Application Data

(60) Provisional application No. 63/134,386, filed on Jan. 6, 2021.

(51) Int. Cl.
*B25B 27/14* (2006.01)
*B05B 15/60* (2018.01)

(52) U.S. Cl.
CPC .............. *B25B 27/14* (2013.01); *B05B 15/60* (2018.02)

(58) Field of Classification Search
CPC ......... B25B 27/14; B25B 13/06; B05B 15/60; B05B 7/2475; B05B 5/043; B05B 5/1691; B05B 9/0426; B05B 7/0075; B05B 13/0278; A61L 2202/11; A61L 2202/15; A61L 2/22
See application file for complete search history.

(56) References Cited

U.S. PATENT DOCUMENTS

| 4,219,161 A | 8/1980 | Freissle |
| 4,533,005 A | 8/1985 | Morris |
| 4,583,694 A | 4/1986 | Williams et al. |

(Continued)

FOREIGN PATENT DOCUMENTS

| CN | 104289349 B | 8/2016 |
| DE | 20203740 U1 | 5/2002 |

(Continued)

OTHER PUBLICATIONS

Extended European Search Report for Application No. 21217273.8 dated Jun. 2, 2022 (8 pages).

*Primary Examiner* — Rick K Chang
(74) *Attorney, Agent, or Firm* — Michael Best & Friedrich LLP (57) ABSTRACT

The present disclosure is directed to a tool for operating a nozzle holder. The nozzle holder is configured to couple a spray nozzle to a spray device, and includes an outer ring movable between a holding position and a release position. The nozzle holder is configured to securely hold the spray nozzle when the outer ring is in the holding position, and release the spray nozzle when the outer ring is in the release position. The tool includes an elongated body including a first end that defines an annular rim and a pocket that communicates with the annular rim. The annular rim is configured to selectively engage the outer ring to move the outer ring from the holding position to the release position. The elongated body also includes a second end that defines a recess configured to selectively receive and hold a portion of the spray nozzle.

22 Claims, 8 Drawing Sheets

(56) References Cited

U.S. PATENT DOCUMENTS

| | | |
|---|---|---|
| 5,337,958 A | 8/1994 | Hennessy et al. |
| 5,421,522 A | 6/1995 | Bowen |
| 5,479,670 A | 1/1996 | Coffey |
| 6,216,959 B1 | 4/2001 | Garrison et al. |
| 6,234,411 B1 | 5/2001 | Walker et al. |
| 6,969,057 B2 | 11/2005 | Baltz et al. |
| 7,458,524 B2 | 12/2008 | Prieto et al. |
| 7,648,086 B2 | 1/2010 | Struck |
| 7,770,815 B2 | 8/2010 | Green et al. |
| 8,308,083 B2 | 11/2012 | Woodgate et al. |
| 8,590,810 B2 | 11/2013 | Woodgate et al. |
| 8,672,243 B2 | 3/2014 | Turcic et al. |
| 9,283,574 B2 | 3/2016 | Leistiko |
| 9,303,393 B2 | 4/2016 | Bush |
| 10,035,161 B2 | 7/2018 | Robert |
| 10,087,609 B2 | 10/2018 | Bush |
| 10,137,468 B2 | 11/2018 | Robert |
| 10,322,424 B2 | 6/2019 | Wright |
| 10,378,192 B2 | 8/2019 | Bush |
| 10,434,533 B2 | 10/2019 | Robert |
| 10,589,298 B2 | 3/2020 | Wright |
| 2007/0257138 A1 | 11/2007 | Riese |
| 2010/0270337 A1 | 10/2010 | Green et al. |
| 2010/0327086 A1 | 12/2010 | Hassler |
| 2012/0031993 A1 | 2/2012 | Leistiko |
| 2013/0245576 A1 | 9/2013 | Hoogenakker et al. |
| 2013/0327850 A1 | 12/2013 | Joseph et al. |
| 2016/0221160 A1* | 8/2016 | Boland .............. B25B 13/06 |
| 2017/0173607 A1 | 6/2017 | Wright |
| 2018/0178226 A1 | 6/2018 | Morgan et al. |
| 2019/0060922 A1 | 2/2019 | Wright |
| 2020/0023384 A1 | 1/2020 | Ketterer |
| 2020/0121867 A1 | 4/2020 | Wright |
| 2020/0238308 A1 | 7/2020 | Forgey et al. |
| 2020/0384616 A1* | 12/2020 | Anex ............. B25B 23/0035 |

FOREIGN PATENT DOCUMENTS

| | | |
|---|---|---|
| WO | 2015051385 A1 | 4/2015 |
| WO | 2020005691 A1 | 1/2020 |

* cited by examiner

//TOOL FOR POWERED SPRAYER

CROSS-REFERENCE TO RELATED APPLICATIONS

This application claims priority to co-pending U.S. Provisional Patent Application No. 63/134,386, filed Jan. 6, 2021, the entire content of which is hereby incorporated by reference.

FIELD OF THE DISCLOSURE

The present invention relates to powered sprayers, and more particularly to tools for operating a nozzle of a powered sprayer.

BACKGROUND OF THE DISCLOSURE

A powered sprayer can include a removable nozzle. A tool can facilitate removing or installing the nozzle in the powered sprayer.

SUMMARY OF THE DISCLOSURE

The present disclosure provides, in one aspect, a tool for operating a nozzle holder, the nozzle holder configured to selectively and removably couple a spray nozzle to a spray device. The nozzle holder includes an outer ring movable between a holding position and a release position. The nozzle holder is configured to securely hold the spray nozzle when the outer ring is in the holding position. The nozzle holder is configured to release the spray nozzle when the outer ring is in the release position. The tool includes an elongated body including a first end that defines an annular rim and a pocket that communicates with the annular rim, the annular rim being configured to selectively engage the outer ring to move the outer ring from the holding position to the release position. The elongated body also includes a second end opposite the first end, the second end defining a recess configured to selectively receive and hold a portion of the spray nozzle.

The present disclosure provides, in another aspect, a tool for operating a nozzle holder, the nozzle holder configured to selectively and removably couple a spray nozzle to a spray device. The tool includes an elongated body extending between a first end and a second end opposite the first end. The second end defines a recess configured to selectively receive and hold a portion of the spray nozzle. The tool also includes a nozzle storage receptacle formed in the body between the first end and the second end, the nozzle storage receptacle configured to selectively receive and hold the spray nozzle. The nozzle storage receptacle defines an aperture that extends through the body between a first lateral side of the body and a second lateral side of the body opposite the first lateral side.

The present disclosure provides, in another aspect, a method for operating a nozzle holder with a tool. The nozzle holder is configured to selectively couple a spray nozzle to a spray device. The nozzle holder includes an outer ring movable between a holding position and a release position. The nozzle holder is configured to securely hold the spray nozzle when the outer ring is in the holding position. The nozzle holder is configured to release the spray nozzle when the outer ring is in the release position. The spray device includes a tube that surrounds the nozzle holder, the tube defining an opening. The tool includes an elongated body extending between a first end and a second end opposite the first end, the first end defining a pocket. The method includes inserting the first end of a tool through the opening. The method also includes pressing the first end against the outer ring to retract the outer ring from the holding position to the release position, causing nozzle holder to release the spray nozzle. The method further includes receiving the spray nozzle into the pocket defined in the first end. The method also includes removing the first end of the tool from the opening to retrieve the spray nozzle.

Other aspects of the disclosure will become apparent by consideration of the detailed description and accompanying drawings.

Before any embodiments of the application are explained in detail, it is to be understood that the application is not limited in its application to the details of construction and the arrangement of components set forth in the following description or illustrated in the following drawings. The application is capable of other embodiments and of being practiced or of being carried out in various ways.

DETAILED DESCRIPTION

Figure 1:
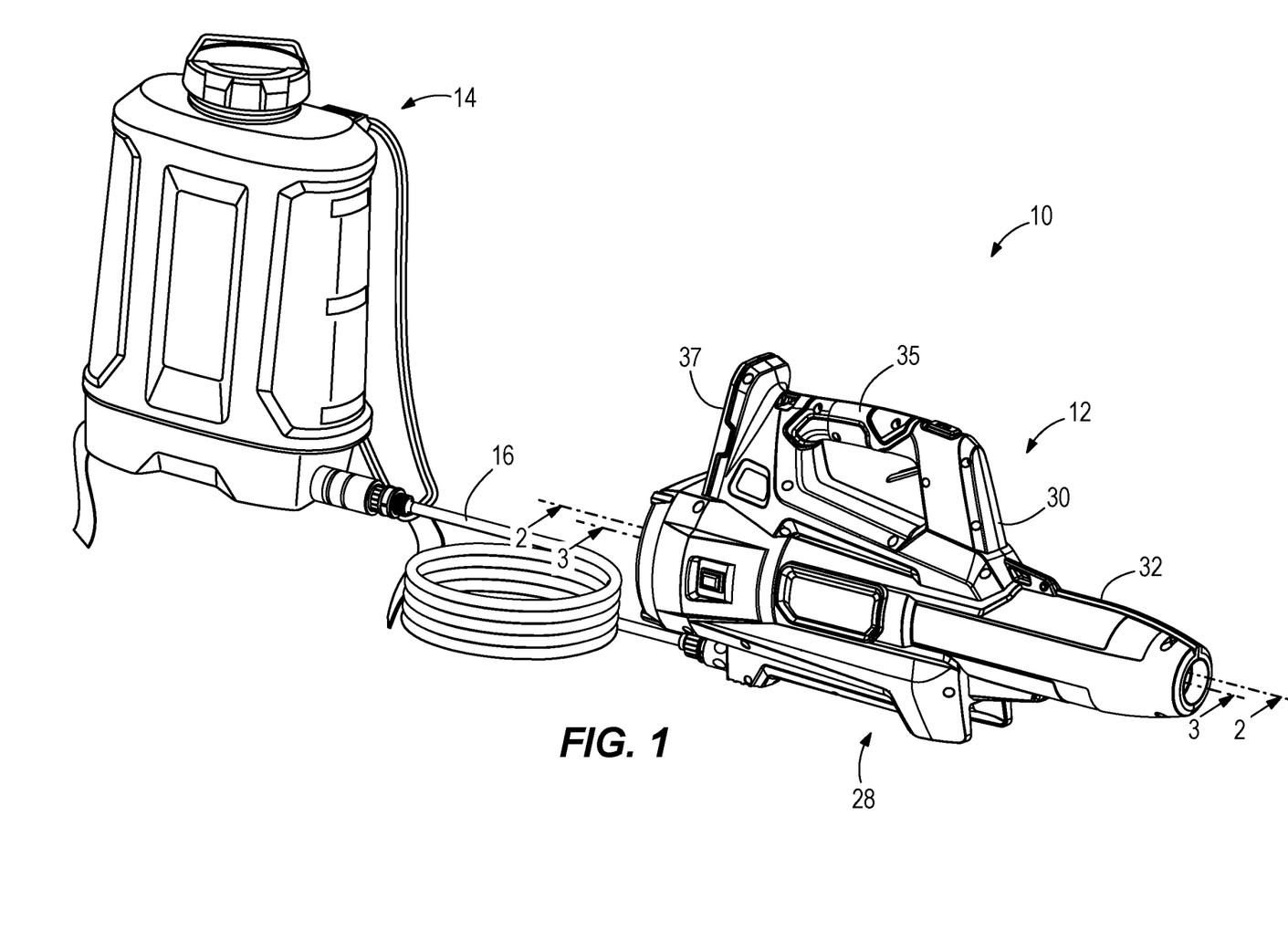
FIG. 1 is a perspective view of a fogger according to an embodiment of the disclosure.
Figure 2:
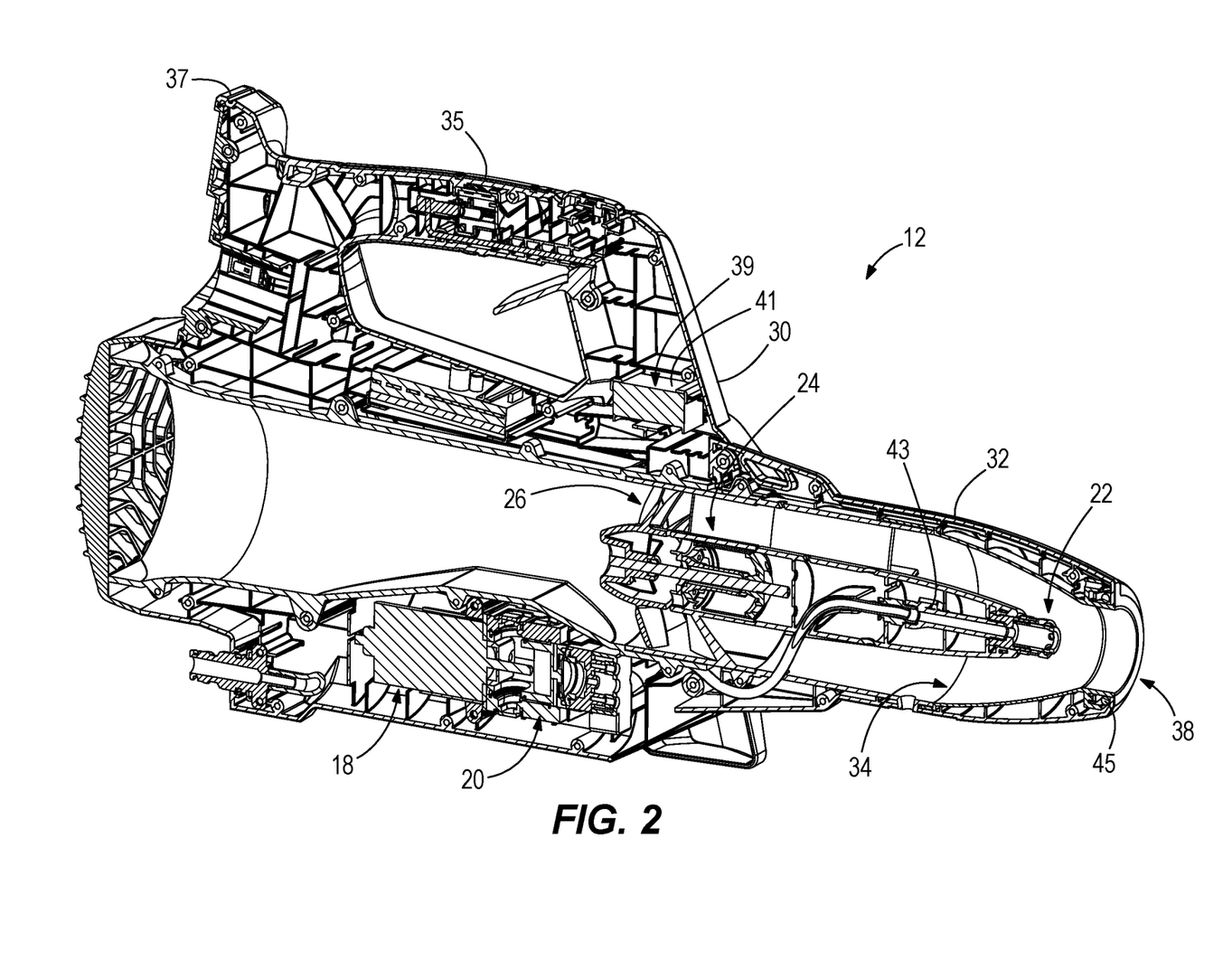
FIG. 2 is a perspective cross-sectional view of a sprayer unit of the fogger of FIG. 1, taken along line 2-2 of FIG. 1.

FIGS. 1 and 2 illustrate a spray device configured as an electrostatic powered sprayer or fogger 10 for spraying a fine mist of atomized liquid disinfecting solution to disinfect surfaces. The fogger 10 includes a handheld sprayer unit 12 fluidly coupled to a remote reservoir 14 via a hose 16. The sprayer unit 12 includes a first motor 18 that drives a liquid pump 20 to draw the liquid solution from the reservoir 14 and direct the solution through an atomizing nozzle assembly 22. The sprayer unit 12 also includes a second motor 24 that drives a blower 26 to direct an airflow past the nozzle assembly 22 to increase the throw of the atomized solution.

The sprayer unit 12 further includes a housing 28 that includes a main housing 30 in which the motor 18 and pump 20 are supported, and a tube 32 that defines an airflow channel 34. The main housing 30 defines a handle portion 35 that may be grasped by the user during use to manipulate the orientation and position of the sprayer unit 12. The main housing 30 also defines a battery receptacle 37 that selectively couples to a removable and rechargeable battery pack (not shown) to provide DC electrical power to the sprayer 10. In alternative embodiments, the sprayer 10 may be AC powered (e.g., plugged into a standard home electrical socket).

Figure 3:
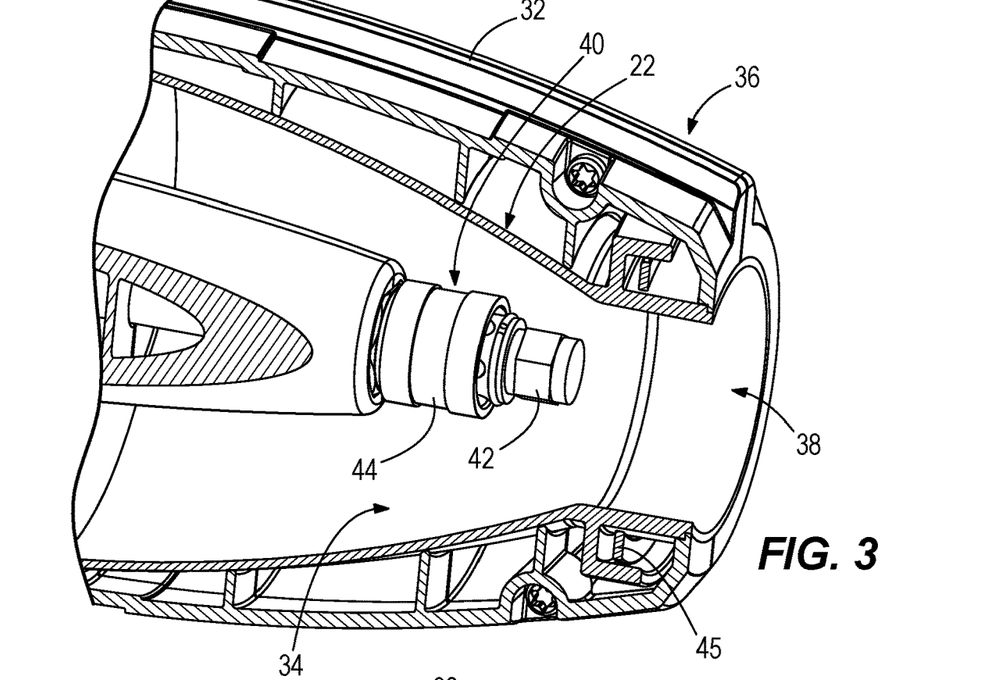
FIG. 3 is a perspective cross-sectional view of portions of the sprayer unit of FIG. 2, taken along line 3-3 of FIG. 1.

With reference to FIGS. 2 and 3, the sprayer 10 also includes an electrostatic charging circuit 39 operable to impart an electrostatic charge in the atomized liquid droplets exiting the nozzle assembly 22 during operation of the sprayer 10. The electrostatic charging circuit 39 includes a high voltage supply module 41 supported within the main housing 30, a first or high voltage electrode assembly 43 positioned in-line between the pump 20 and the nozzle assembly 22, and a second electrode assembly or grounding ring assembly 45 suspended in front of the nozzle assembly 22. The high voltage supply module 41 receives power from the battery pack and supplies power to the high voltage electrode assembly 43. The grounding ring assembly 45 is electrically coupled to the high voltage supply module 41 to complete the charging circuit 39. During operation of the sprayer 10, the liquid solution passes through the high voltage electrode assembly 43 and is directly charged by direct contact therewith. An electric field develops between the grounding ring assembly 45 and any conductive material (such as, e.g., the liquid solution) in electrical contact with the high voltage electrode assembly 43. As the atomized spray droplets of the liquid solution exit the nozzle assembly 22, the droplets pass through the interior of the grounding ring assembly 45 and through the electric field, thereby acquiring an electrostatic charge. The acquired charge enables the spray droplets to better adhere or "stick" to targeted surfaces.

Figure 4:
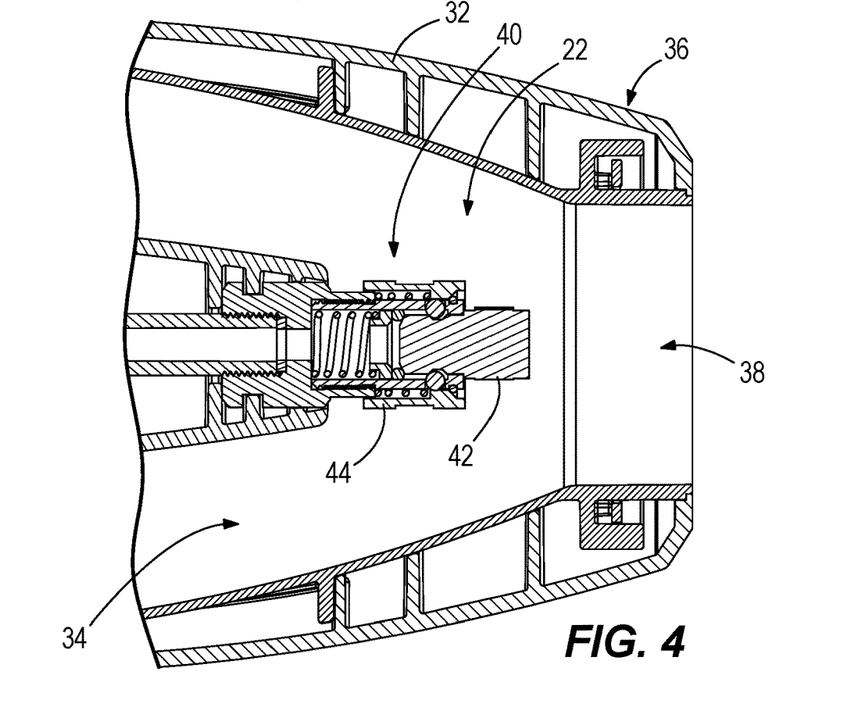
FIG. 4 is a cross-sectional view of portions of the sprayer unit of FIG. 2, taken along line 2-2 of FIG. 1.
Figures 5, 6, 7:
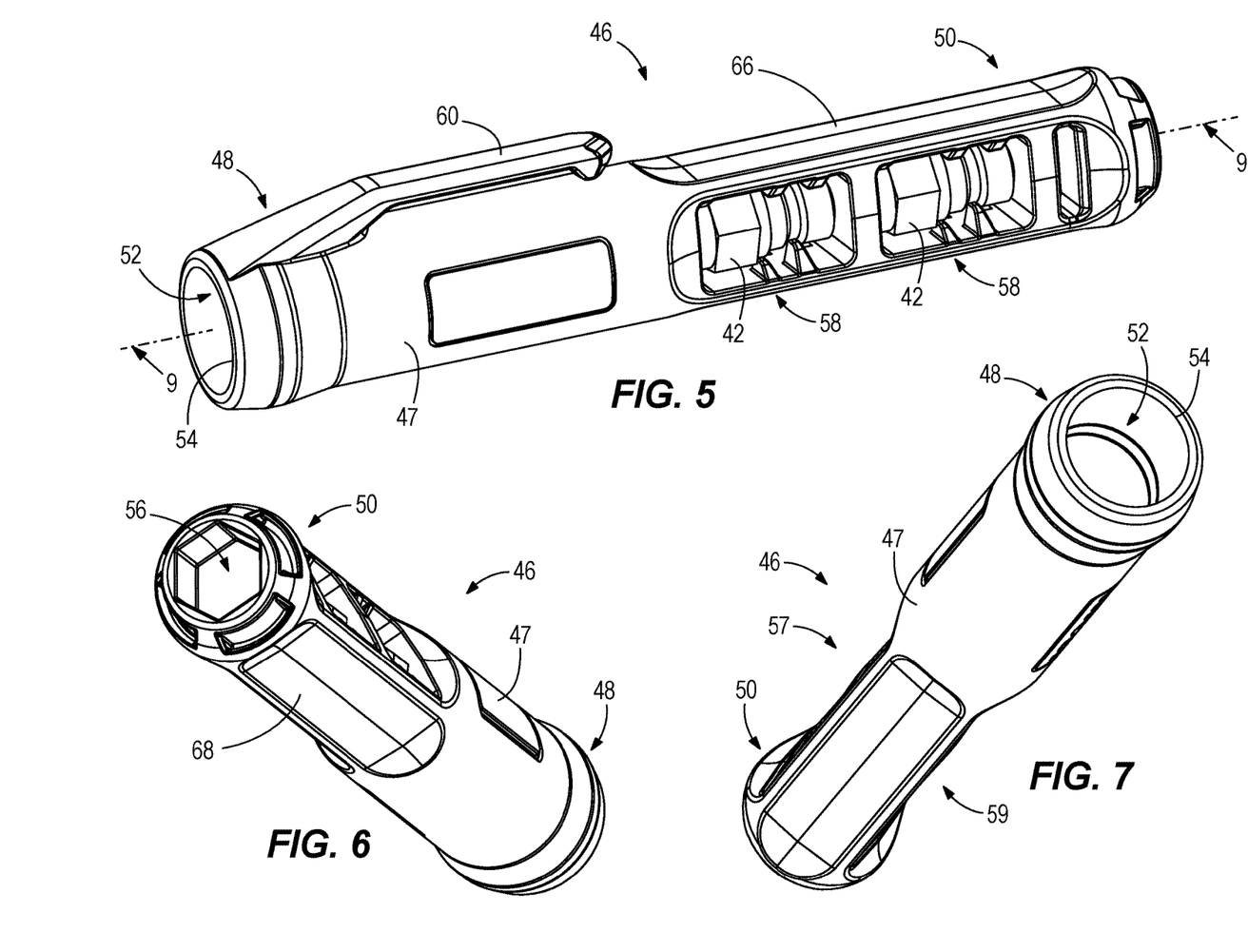
FIGS. 5-7 are perspective views of a tool for operating a nozzle holder of the fogger of FIG. 1.
Figure 8:
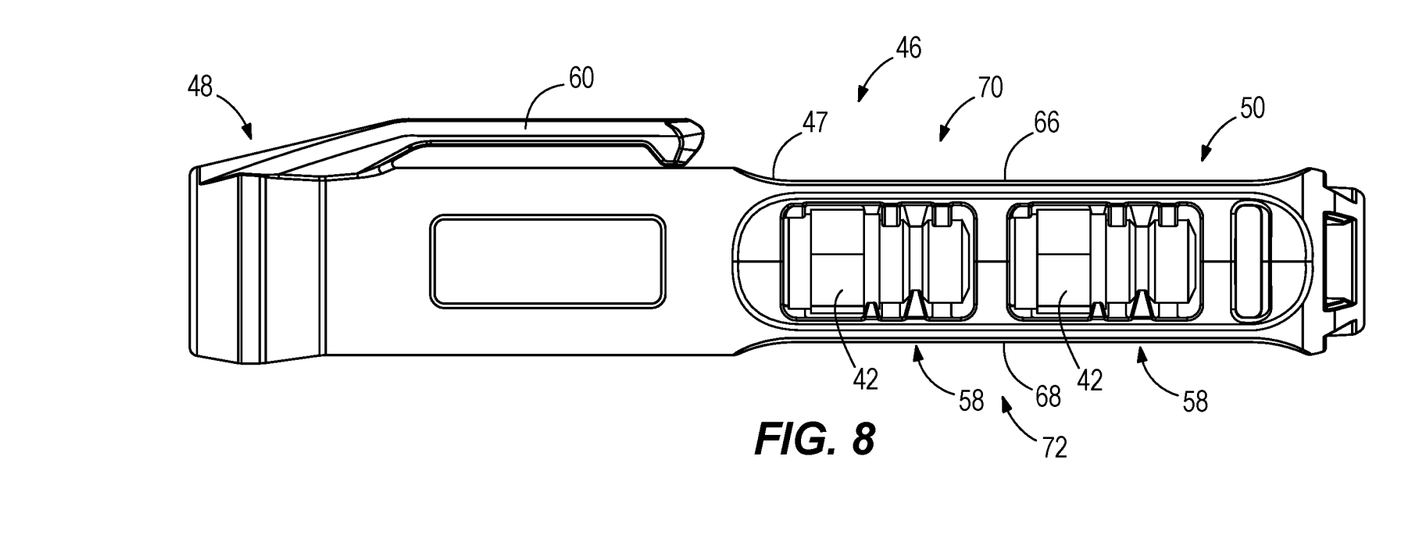
FIG. 8 is a side view of the tool of FIG. 5.
Figure 9:
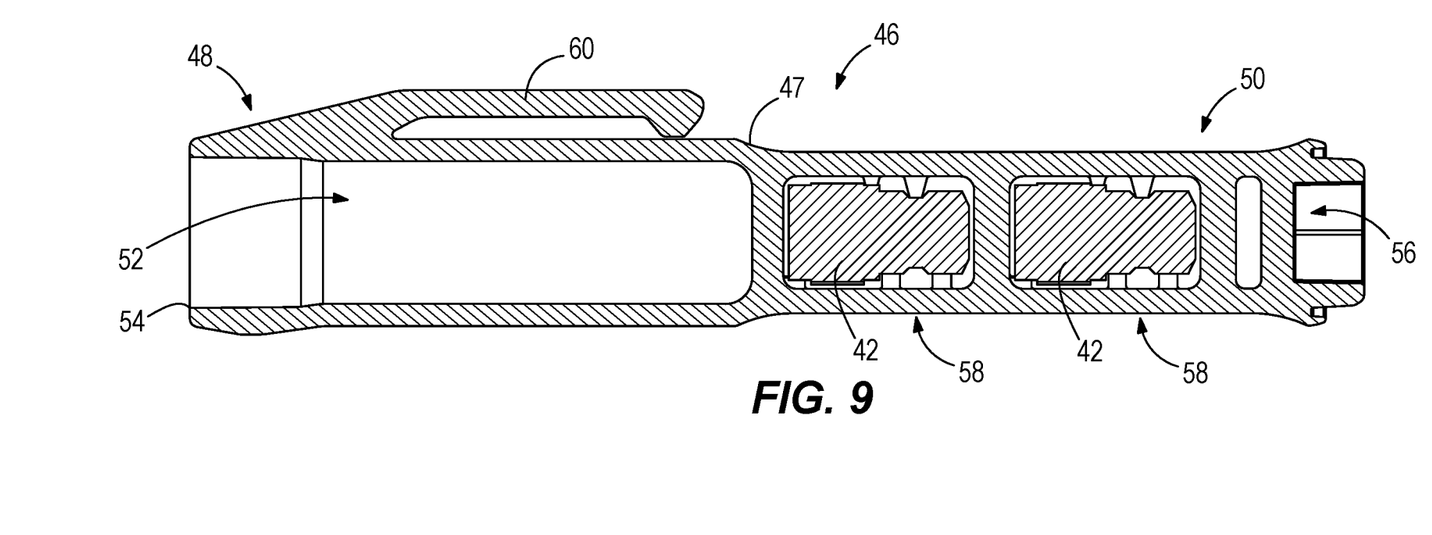
FIG. 9 is a cross-sectional view of the tool of FIG. 5, taken along line 9-9 of FIG. 5.

The nozzle assembly 22 is suspended within the tube 32 proximate a forward end 36 that defines an outlet opening 38. The nozzle assembly 22 includes a quick-connect nozzle holder 40 and a removable, replaceable nozzle 42. The nozzle 42 can be removed from the nozzle holder 40 (e.g., for cleaning) and can also be replaced with a different nozzle (e.g., having different spray characteristics). Specifically, the nozzle holder 40 includes a retractable outer ring 44 that is movable between a holding position (FIG. 4), in which the nozzle 42 is securely held within the nozzle holder 40, and a release position (FIGS. 10B and 10C), in which the nozzle 42 is released and ejected from the nozzle holder 40. In other embodiments (not shown), the nozzle holder 40 can receive and hold the nozzle by other means. For example, the nozzle holder 40 can include internal threads for threadably receiving an externally threaded nozzle. In In another example, the nozzle holder 40 can receive the nozzle in a bayonet lock arrangement.

Since the nozzle assembly 22 resides within the tube 32, it must be accessed through the outlet opening 38 to remove or replace the nozzle 42. Accordingly, FIGS. 5-9 illustrate a tool 46 for removing or installing the nozzle 42 at the nozzle holder 40. The tool 46 has a generally elongated rod-like body 47 that includes a first end or removal end 48, and an opposite second end or installation end 50. The removal end 48 defines a pocket 52 (FIG. 9) and includes an annular rim 54 communicating with the pocket 52 and having a diameter corresponding to a diameter of the retractable outer ring 44 of the nozzle holder 40. The installation end 50 defines a recess 56 having a size and shape corresponding to the size and shape of a front portion of the nozzle 42. In the illustrated embodiment, the recess 56 has a hexagonal shape corresponding to the hexagonal shape of the front portion of the nozzle 42. The recess 56 receives the front portion of the nozzle 42 (e.g., by nominal slip fit) to temporarily hold the nozzle 42 so that it may be subsequently installed into the nozzle holder 40 using the tool 46.

The tool 46 also includes nozzle storage receptacles 58 formed in a central region of the body 47 between the removal and installation ends 48, 50. The storage receptacles 58 receive additional nozzles 42 for storage and safekeeping. In the illustrated embodiment, the storage receptacles 58 define respective apertures that extend all the way through the body 47 between opposite first and second lateral sides 57, 59 of the body 47. As such, nozzle 42 may be inserted into each storage receptacle 58 from the first lateral side 57 or from the second lateral side 59. In other embodiments (not shown), the storage receptacles may instead define recesses that are open to only one of the lateral sides 57, 59 and are closed to the other lateral side 57, 59.

Figure 12:
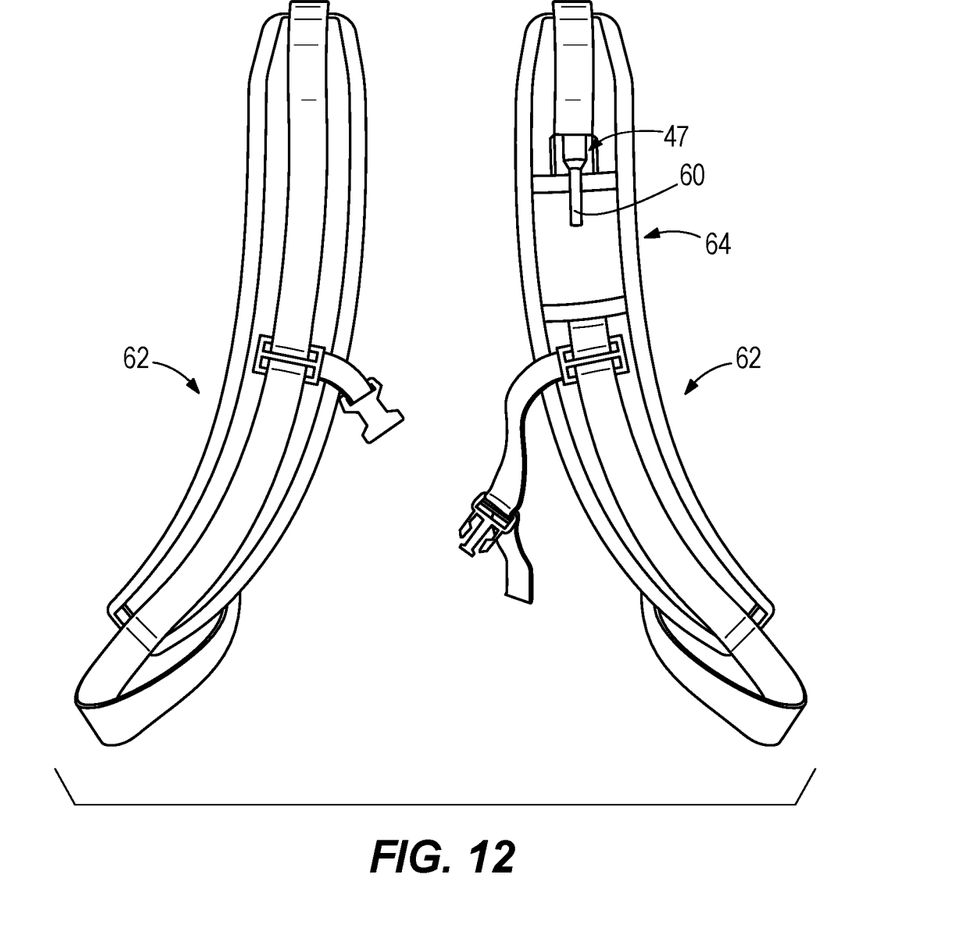
FIG. 12 illustrates a pair of backpack straps that can be attached to a backpack for carrying a remote reservoir of the fogger of FIG. 1.

The tool 46 further includes a flexible arm or clip 60 extending from the body 47 that allows the tool 46 to be secured to an article such as a belt, a strap, a pocket, or the like. For example, FIG. 12 illustrates a pair of backpack straps 62 that can be attached to a backpack for carrying the remote reservoir 14 (FIG. 1). The backpack straps 62 include a pocket 64, and the tool 46 is shown secured to the rim of the pocket 64 via the clip 60. In the illustrated embodiment, the clip 60 is integrally formed with the body 47. In other embodiments (not shown), the clip 60 can be a separate component affixed to the body 47.

The tool 46 further includes first and second planer grip surfaces 66, 68 formed at opposite top and bottom sides 70, 72 of the body 47. The grip surfaces 66, 68 are also formed in the central region of the body 47 and located adjacent the storage receptacles 58. The grip surfaces 66, 68 can be grasped by the user to hold and manipulate the tool 46.

Figure 10A:
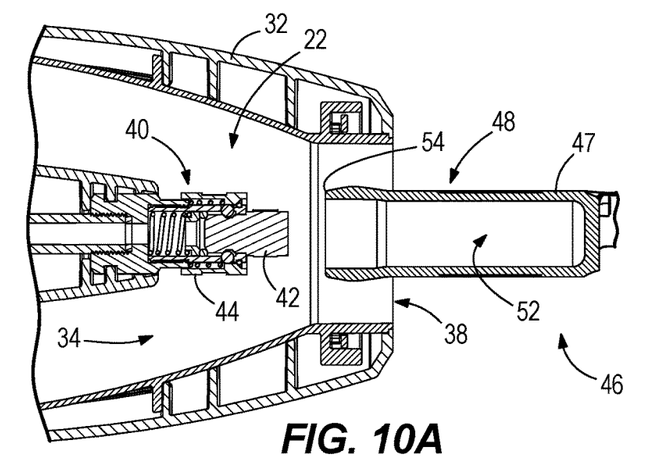
FIGS. 10A-10C are cross-sectional views of portions of the sprayer unit of FIG. 2 and of the tool of FIG. 5, illustrating a process for removing a spray nozzle from the nozzle holder using the tool.
Figure 10B:
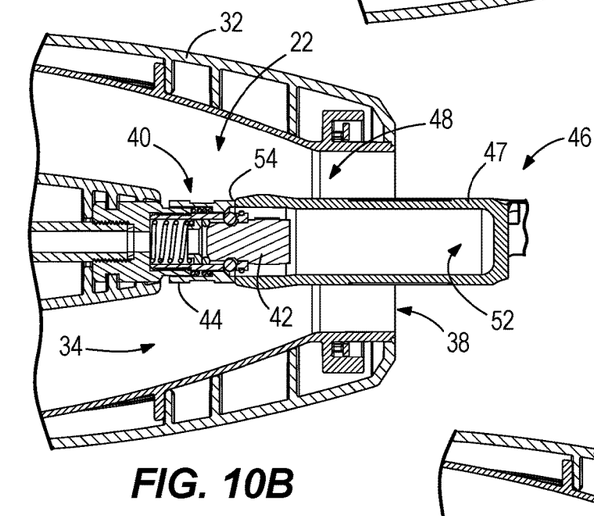
Figure 10C:
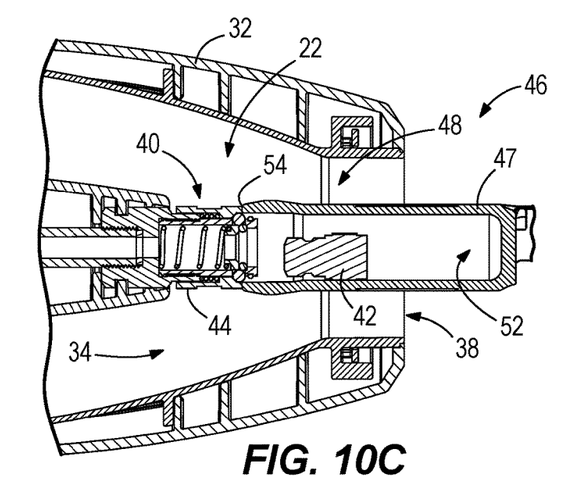

FIGS. 10A-10C illustrate a process for removing the nozzle 42 from the nozzle holder 40 using the tool 46. With reference to FIG. 10A, the removal end 48 of the tool 46 is first inserted into the tube 32 through the outlet opening 38. With reference to FIG. 10B, the annular rim 54 is moved over the nozzle 42 and pressed against the outer ring 44, causing the outer ring 44 to retract from the holding position (FIG. 10A) to the release position (FIG. 10B). With the outer ring 44 retracted, the nozzle 42 is released and ejected from the nozzle holder 40 (FIG. 10C). The ejected nozzle 42 lands within the pocket 52. The tool 46 can then be removed from the tube 32 and the nozzle 42 retrieved from within the pocket 52.

Figures 11A, 11B, 11C:
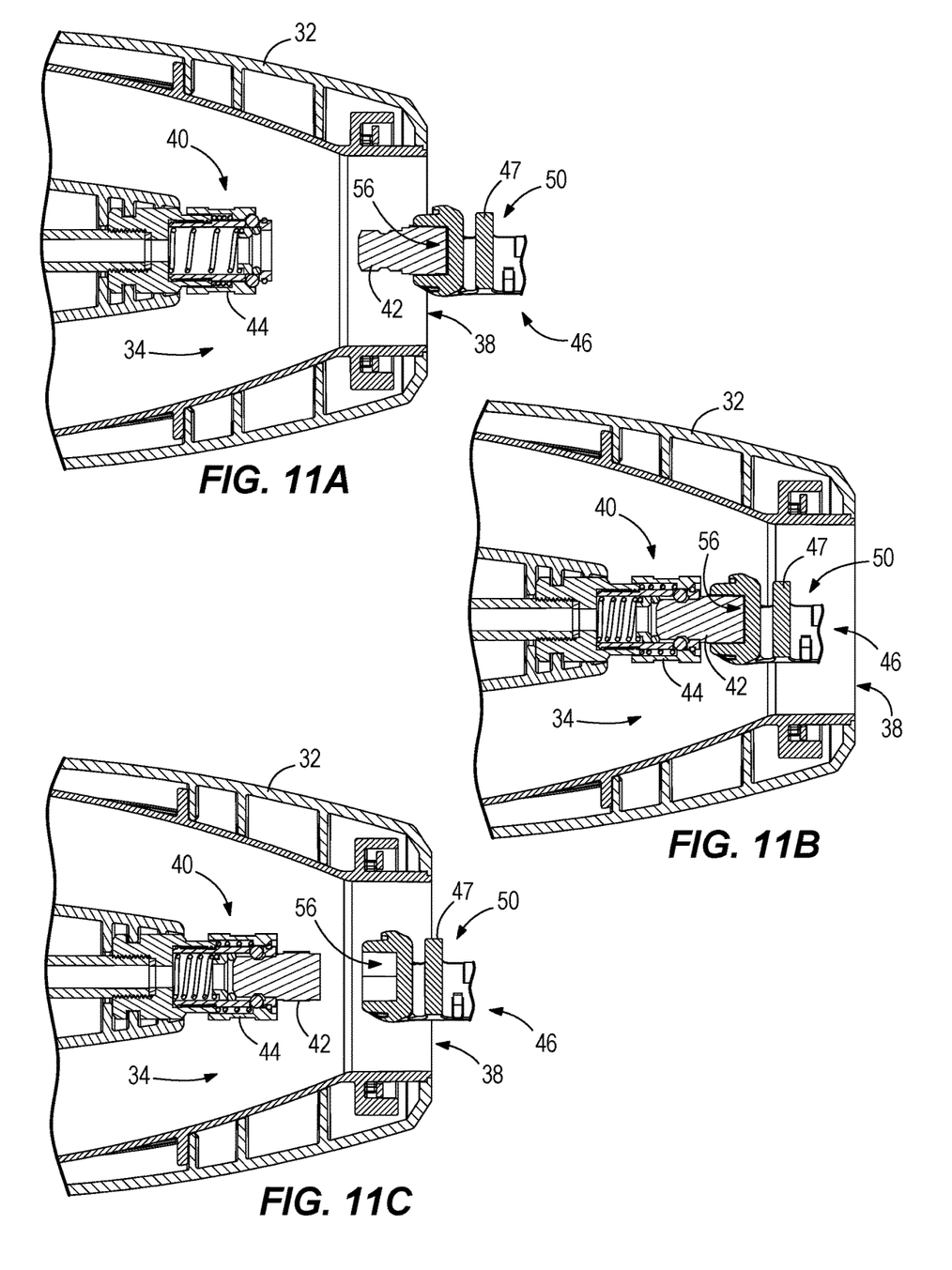
FIGS. 11A-11C are cross-sectional views of portions of the sprayer unit of FIG. 2 and of the tool of FIG. 5, illustrating a process for installing the spray nozzle into the nozzle holder using the tool.

FIGS. 11A-11C illustrate a process for installing the nozzle 42 into the nozzle holder 40 using the tool 46. With reference to FIG. 11A, the front portion of the nozzle 42 is inserted into the recess 56 of the installation end 50 of the tool 46, and the installation end 50 is inserted into the tube 32 through the outlet opening 38. With reference to FIG. 11B, the opposite end of the nozzle 42 is then pressed into the nozzle holder 40 until it reaches a secured position at which the outer ring 44 moves to the holding position (FIG. 11B). With the nozzle 42 secured within the nozzle holder 40, the tool 46 can then be removed from the tube 32 (FIG. 11C).

Various features of the disclosure are set forth in the following claims.

What is claimed is:

1. A tool for operating a nozzle holder, the nozzle holder configured to selectively and removably couple a spray nozzle to a spray device, the nozzle holder including an outer ring movable between a holding position and a release position, the nozzle holder being configured to securely hold the spray nozzle when the outer ring is in the holding position, and the nozzle holder being configured to release the spray nozzle when the outer ring is in the release position, the tool comprising:
an elongated body including
a first end that defines a circular rim and a pocket that communicates with the circular rim, the circular rim being configured to selectively engage the outer ring to move the outer ring from the holding position to the release position, and
a second end opposite the first end, the second end defining a recess configured to selectively receive and hold a portion of the spray nozzle.

2. The tool of claim 1, further comprising a nozzle storage receptacle formed in the body between the first end and the second end, the nozzle storage receptacle configured to selectively receive and hold the spray nozzle.

3. The tool of claim 2, wherein the nozzle storage receptacle is a first nozzle storage receptacle, and the tool further includes a second nozzle storage receptacle formed in the body between the first end and the second end and configured to selectively receive and hold the spray nozzle.

4. The tool of claim 2, wherein the nozzle storage receptacle defines an aperture that extends through the body between a first lateral side of the body and a second lateral side of the body opposite the first lateral side.

5. The tool of claim 2, further comprising a pair of planar grip surfaces formed on the body between the first end and the second end.

6. The tool of claim 5, wherein the pair of planar grip surfaces are located adjacent the nozzle storage receptacle.

7. The tool of claim 2, wherein the nozzle storage receptacle is located between the pocket and the recess.

8. The tool of claim 1, further comprising a flexible arm extending from the body.

9. The tool of claim 1, wherein the recess includes a hexagonal shape that corresponds to a hexagonal shape of the portion of the spray nozzle.

10. A tool for operating a nozzle holder, the nozzle holder configured to selectively and removably couple a spray nozzle to a spray device, the tool comprising:
an elongated body extending between a first end and a second end opposite the first end, the second end defining a recess configured to selectively receive and hold a portion of the spray nozzle;
a first nozzle storage receptacle formed in the body between the first end and the second end, the first nozzle storage receptacle configured to selectively receive and hold the spray nozzle; and
a second nozzle storage receptacle formed in the body between the first end and the second end, the second nozzle storage receptacle configured to selectively receive and hold the spray nozzle;
wherein the first nozzle storage receptacle defines an aperture that extends through the body between a first lateral side of the body and a second lateral side of the body opposite the first lateral side.

11. The tool of claim 10, wherein the first end defines an annular rim and a pocket that communicates with the annular rim, the annular rim being configured to selectively engage the nozzle holder to release the spray nozzle from the nozzle holder.

12. The tool of claim 10, further comprising a flexible arm extending from the body.

13. The tool of claim 10, further comprising a pair of planar grip surfaces formed on the body between the first end and the second end.

14. The tool of claim 13, wherein the pair of planar grip surfaces are located adjacent the first nozzle storage receptacle.

15. The tool of claim 10, wherein the recess includes a hexagonal shape that corresponds to a hexagonal shape of the portion of the spray nozzle.

16. A method for operating a nozzle holder with a tool, the nozzle holder being configured to selectively couple a spray nozzle to a spray device, the nozzle holder including an outer ring movable between a holding position and a release position, the nozzle holder being configured to securely hold the spray nozzle when the outer ring is in the holding position, and the nozzle holder being configured to release the spray nozzle when the outer ring is in the release position, the spray device including a tube that surrounds the nozzle holder, the tube defining an opening, and the tool including an elongated body extending between a first end and a second end opposite the first end, the first end defining a pocket, the method comprising:
inserting the first end of the tool through the opening;
pressing the first end against the outer ring to retract the outer ring from the holding position to the release position, causing nozzle holder to release the spray nozzle;
receiving the spray nozzle into the pocket defined in the first end; and
removing the first end of the tool from the opening to retrieve the spray nozzle.

17. The method of claim 16, further comprising inserting the spray nozzle into a nozzle storage receptacle defined in the body of the tool between the first end and the second end.

18. The method of claim 16, wherein the spray nozzle is a first spray nozzle, and wherein the method further comprises inserting a portion of a second spray nozzle into a recess defined in the second end of the tool.

19. The method of claim 18, further comprising:
inserting the second end of the tool through the opening; and
pressing the second spray nozzle into the nozzle holder to secure the second spray nozzle in the nozzle holder.

20. The method of claim 16, wherein the spray nozzle is a first spray nozzle, and wherein the method further comprises removing a second spray nozzle from a nozzle storage receptacle defined in the body of the tool between the first end and the second end.

21. The tool of claim 11, wherein the nozzle storage receptacle is located between the pocket and the recess.

22. The tool of claim 11, wherein the annular rim is circular.

* * * * *